US010517197B2

(12) United States Patent
McGhee

(10) Patent No.: US 10,517,197 B2
(45) Date of Patent: Dec. 24, 2019

(54) SHIELDED ISOLATION CHAMBER

(71) Applicant: David McGhee, Monument, CO (US)

(72) Inventor: David McGhee, Monument, CO (US)

(*) Notice: Subject to any disclaimer, the term of this patent is extended or adjusted under 35 U.S.C. 154(b) by 0 days.

(21) Appl. No.: 16/179,090

(22) Filed: Nov. 2, 2018

(65) Prior Publication Data
US 2019/0133003 A1 May 2, 2019

Related U.S. Application Data

(60) Provisional application No. 62/580,901, filed on Nov. 2, 2017.

(51) Int. Cl.
H05K 9/00 (2006.01)
A61M 21/00 (2006.01)
A61N 1/16 (2006.01)

(52) U.S. Cl.
CPC ......... H05K 9/0024 (2013.01); H05K 9/0001 (2013.01); H05K 9/0064 (2013.01); H05K 9/0069 (2013.01); A61M 21/0094 (2013.01); A61N 1/16 (2013.01); H05K 9/0081 (2013.01)

(58) Field of Classification Search
CPC ... A61M 21/0094; A61N 1/16; H05K 9/0001; H05K 9/0024; H05K 9/0064; H05K 9/0069; H05K 9/0081
See application file for complete search history.

(56) References Cited

U.S. PATENT DOCUMENTS

| 3,557,777 | A | * | 1/1971 | Cohen ............... A61B 5/04005 |
| | | | | 600/409 |
| 4,000,749 | A | | 1/1977 | Busco |
| 5,042,479 | A | | 8/1991 | Brotz |
| 5,081,071 | A | * | 1/1992 | Hirschkoff ........... H05K 9/0001 |
| | | | | 257/E39.017 |
| 6,140,576 | A | * | 10/2000 | Kanne ................ H05K 9/0001 |
| | | | | 135/136 |
| 6,623,632 | B1 | | 9/2003 | Lipovich |
| 9,364,387 | B2 | | 6/2016 | Hoefler |
| 9,919,162 | B2 | * | 3/2018 | Knight .................... A61N 5/06 |
| 2003/0174487 | A1 | * | 9/2003 | Garmong ............ H05K 9/0001 |
| | | | | 361/816 |

(Continued)

FOREIGN PATENT DOCUMENTS

EP 0128641 A2 12/1984
WO WO 01/32252 * 5/2001

Primary Examiner — James Wu
(74) Attorney, Agent, or Firm — Adsero IP

(57) ABSTRACT

Apparatus and techniques for implementing an isolation chamber, and more particularly for implementing an EMF shielded isolation chamber. In various embodiments, an isolation tank includes a shell having an upper cover and a lower tank portion having one or more sidewalls connected to a floor. The lower tank portion is configured to hold liquid and the lower tank portion and the upper cover together define an interior chamber configured to receive a user. The isolation tank further includes a conductive shield associated with at least a portion of the shell and configured to shield at least a portion of the interior chamber from external electromagnetic fields. In various additional embodiments, the isolation tank includes a shield ground for electrically grounding the shield and/or a liquid ground for electrically grounding the liquid.

12 Claims, 5 Drawing Sheets

(56) References Cited

U.S. PATENT DOCUMENTS

| | | | |
|---|---|---|---|
| 2005/0281957 A1* | 12/2005 | Cooper | A61H 35/00 427/458 |
| 2007/0135676 A1* | 6/2007 | How | A61M 21/0094 600/26 |
| 2011/0245586 A1 | 10/2011 | Slane | |
| 2015/0087893 A1* | 3/2015 | Hill | A61M 21/0094 600/26 |
| 2015/0141741 A1 | 5/2015 | Sullivan | |
| 2015/0357742 A1* | 12/2015 | Lee | H01R 4/66 307/326 |

* cited by examiner

SHIELDED ISOLATION CHAMBER

RELATED APPLICATIONS

This application claims priority to U.S. Provisional Application 62/580,901, filed on Nov. 2, 2017 and titled SHIELDED ISOLATION CHAMBER, which is incorporated herein by reference in its entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

TECHNICAL FIELD

The present disclosure relates to systems, apparatus and methods for implementing an isolation chamber, and more particularly to systems, apparatus and methods for implementing a shielded isolation chamber.

BACKGROUND

Isolation chambers are also commonly called floatation tanks, float tanks, isolation tanks, sensory deprivation tanks, or relaxation tanks. Isolation chambers were created and are used to isolate a person floating in a liquid held inside the tank from sensory stimulation such as sound, sight, and tactile sensations. Floatation tanks hold a person seemingly weightless in a buoyant liquid solution eliminating even the sensation of gravity. Although a person using a conventional isolation chamber is shielded from auditory and optical stimulation, the user may be exposed to electromagnetic fields or electromagnetic radiation having a frequency that can penetrate the typically plastic or fiberglass housing or shell of a conventional isolation chamber. The embodiments disclosed herein are directed toward overcoming one or more of the problems noted above.

SUMMARY

Various embodiments disclosed herein provide improved apparatus and techniques for implementing an isolation chamber. Certain disclosed embodiments provide techniques for implementing a shielded isolation chamber or an isolation chamber with selectable grounding circuits and/or a shield.

The apparatus embodiments disclosed herein are isolation chambers in which a user is isolated from external stimulus. The external stimulus can include, but is not limited to, auditory, visual, tactile, or mechanical stimulus (e.g., vibrations). In addition, certain embodiments include one or more shielding elements or other strategies described herein, to shield the user from electromagnetic fields ("EMFs") or radiation of various types that can propagate through or penetrate the typically fiberglass or plastic exterior shell of a conventional isolation chamber. The disclosed embodiments also may optionally include one or more grounding elements to electrically ground the isolation chamber, the shield of the isolation chamber, the liquid contained within the isolation chamber, and/or the user.

The embodiments disclosed herein include an isolation tank or isolation chamber 100. The apparatus may alternatively be referred to as a flotation tank, flotation chamber, tank, chamber, sensory deprivation tank, sensory deprivation chamber, or the like.

Embodiments of an isolation chamber may include a lower tank portion sized and configured to contain a sufficient quantity of a liquid to float a user in a comfortable supine position. The liquid contained within the lower tank portion is typically water or water with salts dissolved therein to adjust the specific gravity or other attributes of the liquid. The liquid is typically heated with a heater to a comfortable temperature for the user, for example the average surface temperature of the user's skin.

Embodiments of isolation chamber also typically include an upper cover with a door or hatch providing for ingress and egress from the tank. The upper cover also serves to isolate user from sound, light, tactile, or mechanical stimulus. In some embodiments the entire upper cover may be lifted or removed to open the chamber, eliminating the need for a separate door or hatch into the chamber.

In some embodiments, the upper cover and lower tank are separate elements, which can be connected together in use or separated for transportation. In other embodiments, the upper cover and lower tank are a unified structure with the only difference being upper and lower positioning relative to the liquid contained within the isolation tank. In many embodiments disclosed herein, the isolation chamber includes a conductive shield operatively associated with at least a portion of the shell and configured to shield at least a portion of the interior chamber from an external electromagnetic field or undesirable radiation. The shield may be composed of any suitably conductive material including, but not limited to least one of copper, aluminum, gold, silver, iron, nickel, carbon, carbon fiber, alloys or combinations of these materials or similar conductive materials. The shield may be implemented as a mesh, a mesh cloth, a woven cloth, a sheet, a plurality of wires, a wire grid, a plurality of filaments or similar structure. In some embodiments, the shield is integrated into the shell. In other embodiments, the shield is a separate structure from the shell.

Certain embodiments include one or more dedicated grounding circuits, including but not limited to a shield ground electrically coupled to the shield and configured to electrically ground the shield and/or a liquid ground electrically coupled to the liquid in the isolation chamber and configured to electrically ground the liquid. Embodiments within the scope of this disclosure can include any combination of shield and grounding circuits as detailed herein.

Certain embodiments include switches accessible to a user to, for example, selectively connect the shield to a shield ground or disconnect the shield from the shield ground. The same, or a separate user-accessible switch may be included to selectively connect or disconnect the liquid in the isolation chamber to or from a liquid ground. In certain embodiments, the shield ground and liquid ground may be separate physical pathways to earth. In other embodiments the shield ground and liquid ground may be unified. In some embodiments, the shield ground and/or liquid ground are separate from the premises electrical ground which may be connected to electrical appliances such as heaters or pumps associated with the isolation chamber. In other embodiments, the shield ground and liquid ground may share the premises electrical ground with other apparatus.

Various alternative embodiments disclosed herein include methods of implementing, shielding, and/or grounding an isolation chamber as described above.

Various modifications and additions can be made to the embodiments discussed without departing from the scope of the invention. For example, while the embodiments described above refer to particular features, the scope of this invention also includes embodiments having different combination of features and embodiments that do not include all of the above described features.

DETAILED DESCRIPTION

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The embodiments disclosed herein provide isolation chambers, also known as floatation tanks, float tanks, isolation tanks, sensory deprivation tanks, or relaxation tanks, having apparatus to shield the interior of the isolation chamber from external electromagnetic fields ("EMFs") or undesirable radiation that can otherwise penetrate the exterior shell of an unshielded isolation chamber. Alternative embodiments include apparatus to selectively ground the EMF/radiation shield and/or ground the liquid contained within the isolation chamber. Thus, the embodiments disclosed herein may include any combination of EMF or radiation shield and ground, where the shield provides for the attenuation of EMFs or radiation that would otherwise penetrate the interior of the isolation chamber the ground(s) may selectively ground any combination of the shield, the liquid in the isolation chamber, or the user.

Figure 1:
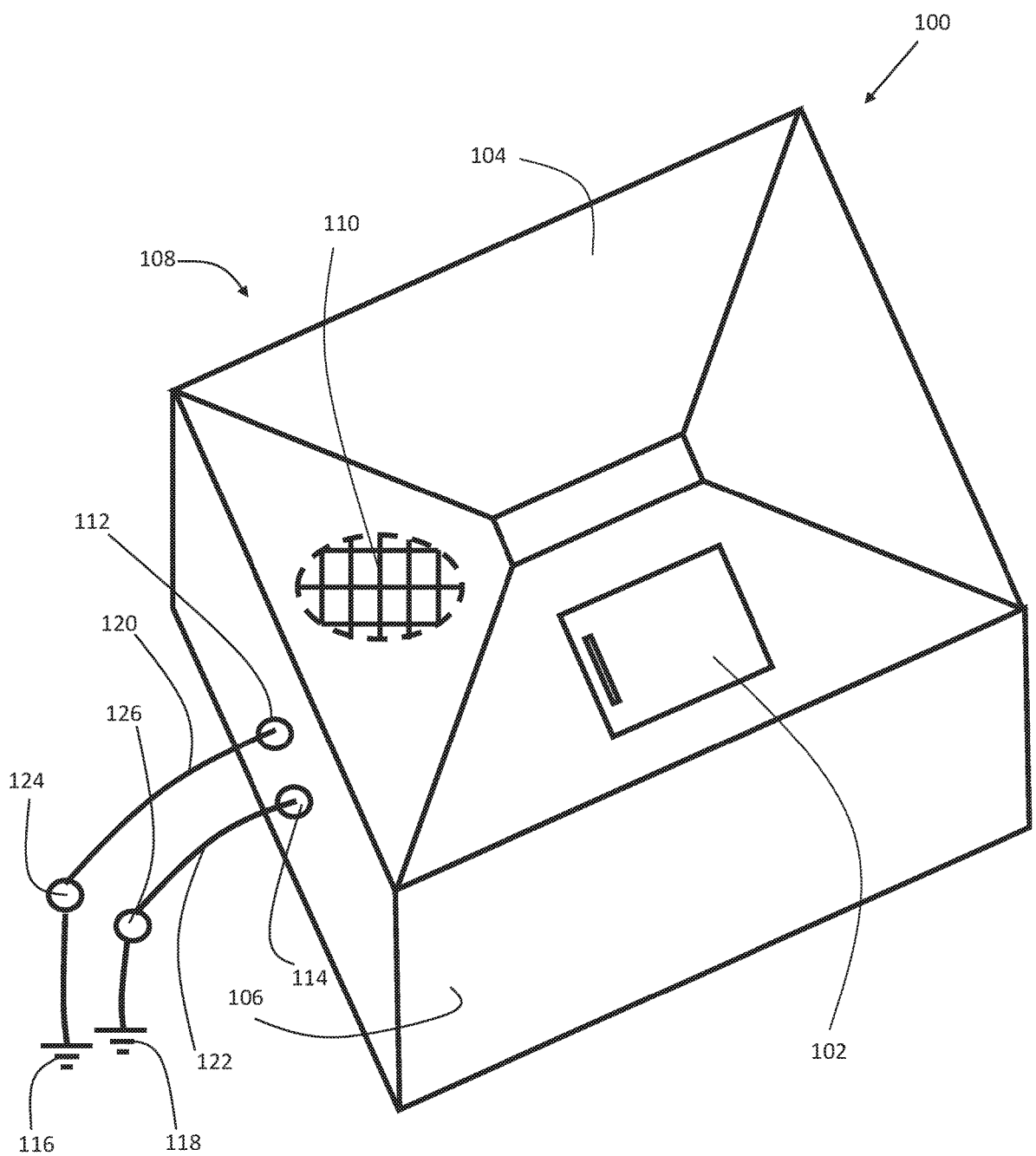
FIG. 1 is a perspective view of an isolation tank, in accordance with various embodiments.

FIG. 1 is a perspective view of a representative isolation tank 100. The isolation tank 100 includes an access door 102, upper walls, cover, or roof 104, and sidewalls 106. The isolation tank 100 also includes a floor (not shown), adjoining the sidewalls 106. The sidewalls 106 and floor together define a lower portion of the isolation tank 100. In alternative embodiments, the cover 104 may be a hinged cover that opens partially or completely, therefore dispensing with the need for an access door 102. In another embodiment, the cover 104, sidewalls 106, and floor may be a unified structure, potentially implemented with curved panels that do not distinctly define separate cover, side wall and floor regions. The interior surfaces of the sidewalls 106 and floor (together defining the lower portion of the isolation tank 100) define a substantially fluid impermeable tank into which floatation liquid 107 (shown in FIGS. 2, 3, and 4) may be placed.

Any liquid placed into the isolation tank 100 is typically, but not necessarily, heated to a desired temperature, for example the exterior body temperature of a user. Heating may be accomplished with any suitable heating apparatus including but not limited to gas or electric powered heaters, solar heating systems or similar apparatus. The floatation liquid 107 can be filtered, circulated, or treated using various apparatus including but not limited to pumps, filters, ozone generating devices, chemical additions and the like. Any electrical element, such as a heater or pump will typically be connected to a ground fault interruption (GFI) circuit as required by local electrical codes. The floatation liquid 107 will typically be water or water with a salt dissolved therein to adjust the specific gravity of the floatation liquid and other attributes. Representative salts that may be dissolved in the floatation liquid 107 include, but are not limited to, magnesium sulfate and sodium chloride.

The upper walls 104, sidewalls 106, floor, access door 102, and any other exterior panel or surface of the isolation tank 100 together define a shell 108 which substantially encloses the interior of the isolation chamber 100. Additionally, the upper walls 104, sidewalls 106, floor, access door 102 and any other exterior structure of the isolation tank 100 together define a chamber and/or interior space within the isolation chamber 100 configured to hold or receive a user. As noted above, in some embodiments, the shell 108 is a unified structure, potentially having curved surfaces that only generally correspond to upper wall, sidewall, floor, cover and other services.

The shell 108 may include or be associated with a shield 110, shielding the interior of the isolation chamber from one or more external electromagnetic fields (EMFs) or from undesirable radiation that would otherwise penetrate or be transmitted through the shell 108 without a shield 110. Thus, the shield 110 attenuates EMFs or radiation within the isolation chamber 100. In some embodiments, the shield 110 is incorporated into the entirety of the top, bottom and sides of the shell 108. Other embodiments may include a partial shield 110. The shield 110 may be fabricated from a conductive material such as copper, aluminum, gold, silver, iron, nickel, another metal, alloys or combinations of metals, carbon, carbon fiber or other conductive or shielding material. The shield 110 may be implemented as a mesh, a mesh cloth, a matt, a foil, a woven cloth, a sheet, a plurality of wires, a grid of wires or other elements, a plurality of filaments or other sheathing. The shield 110 may be applied to the shell 108 at or toward the surface of the shell 108, as a layer positioned within the thickness of the shell 108, distributed throughout the shell, positioned at or toward an interior surface of the shell 108, integrated within the shell 108, or some combination of the above.

Figure 2:
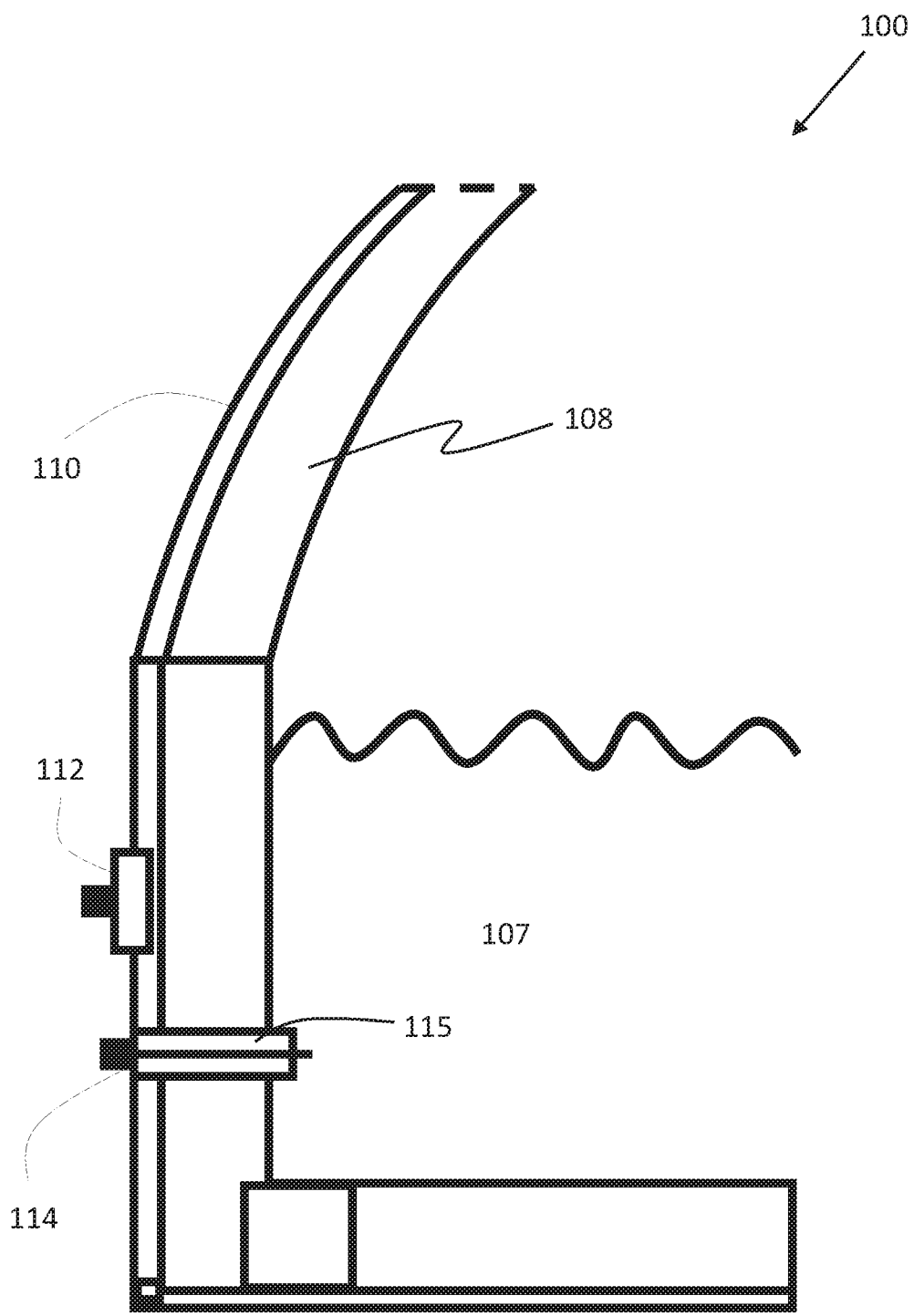
FIG. 2 is a front elevation cross sectional view of an embodiment of an isolation tank.

In some embodiments, the isolation tank 100 may also include one or more shield ground terminals 112 in electrical communication with the shield 110. Electrical communication between the shield 110 and a shield ground terminal 112 may be provided by a soldered connection, a bolted electrical connection, electrically conductive clips or terminals, or any other method providing a relatively low resistance electrical connection between the shield 110 and a shield ground terminal 112. In addition, one or more separate liquid ground terminals 114 may be provided in electrical communication with the floatation liquid 107. Electrical communication between a liquid ground terminal 114 and the floatation liquid 107 may be provided through a conductive probe, conductive plate, conductive surface, wire, or other conductive element extending into contact with the floatation liquid 107. In certain embodiments, any portions of the liquid ground terminal 114 in contact with the floatation liquid 107 are fabricated from a material which resists corrosion, for example stainless steel, titanium, gold plated conductive metal and the like. A representative shield ground terminal 112 and liquid ground terminal 114 are shown in FIG. 2 where the shield ground terminal 112 is in direct electrical contact with the shield 110 on the exterior of the shell 108. The liquid ground terminal 114 extends through the shell but is insulated from the shield 110 by insulating region 115. In many embodiments, the shield ground terminal 112 and the liquid ground terminal 114 are insulated from each other at the shell 108. In other embodiments, the shield ground terminal 112 and the liquid ground terminal 114 are electrically connected to each other at or near the shell 108.

Thus, any shield ground terminal 112 and/or liquid ground terminal 114 may be electrically connected to dedicated grounds away from the isolation chamber 100. See, for example, the dedicated grounds 116 and 118, of FIG. 1 respectively. Dedicated grounds 112, 114 may be implemented with separated ground rods driven into earth or with other known grounding techniques. Alternatively, any shield ground terminal 112 and any liquid ground terminal 114 may be connected to the same physical ground 116, or 118, which may be dedicated to these two ground pathways alone. Alternatively, any shield ground terminal 112 and/or liquid ground terminal 114 may be connected to an existing ground that is not dedicated to the isolation chamber, for example a household ground (not shown on FIG. 1).

The electrical connection between a shield ground terminal 112 or liquid ground terminal 114 and the associated ground may be made using a suitable conductor, for example cables 120 or 122, respectively. As detailed below, the connection between a ground terminal and the associated dedicated or shared ground may optionally be disconnected using a switch, for example switch 124 or 126, respectively.

The shield 110 and associated grounding structures (e.g., shield grounding terminal 112, ground 116, cable 120, switch 124, etc.) may be electrically isolated from the floatation liquid 107. The floatation liquid 107 and associated grounding structures (e.g., liquid grounding terminal 114, ground 118, cable 122, switch 126, etc.) may be electrically isolated from the shield 110. Alternatively, the shield 110 and the floatation liquid 107 may be electrically connected. In some embodiments, a switch, for example switch 124 or 126, respectively, may be provided allowing the user to electrically connect or disconnect the shield 110 and/or floatation liquid 107 from the associated grounds.

Functionally, the shield ground terminal 112 provides a ground path for any current present in, induced into, or conducted into the shield. The liquid ground terminal 114 provides a ground path for any electrical current present in, induced into, or conducted into the liquid 107 and contents immersed in the floatation liquid 107. In some embodiments, a third ground path may be provided that is directly connected to a user, for example with a conductive bracelet or anklet.

Figure 3:
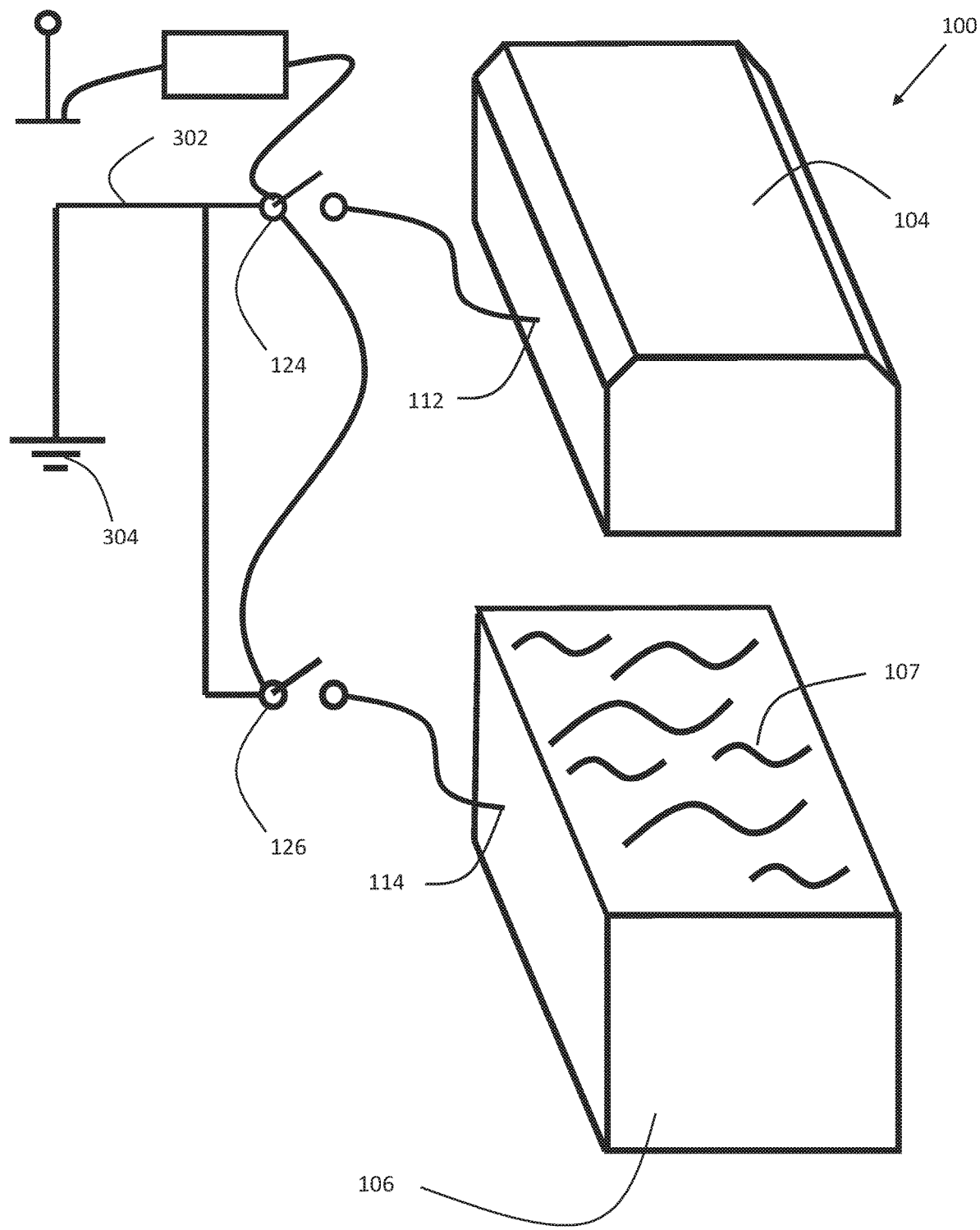
FIG. 3 is a perspective view of an embodiment of an isolation tank showing one grounding circuit.
Figure 4:
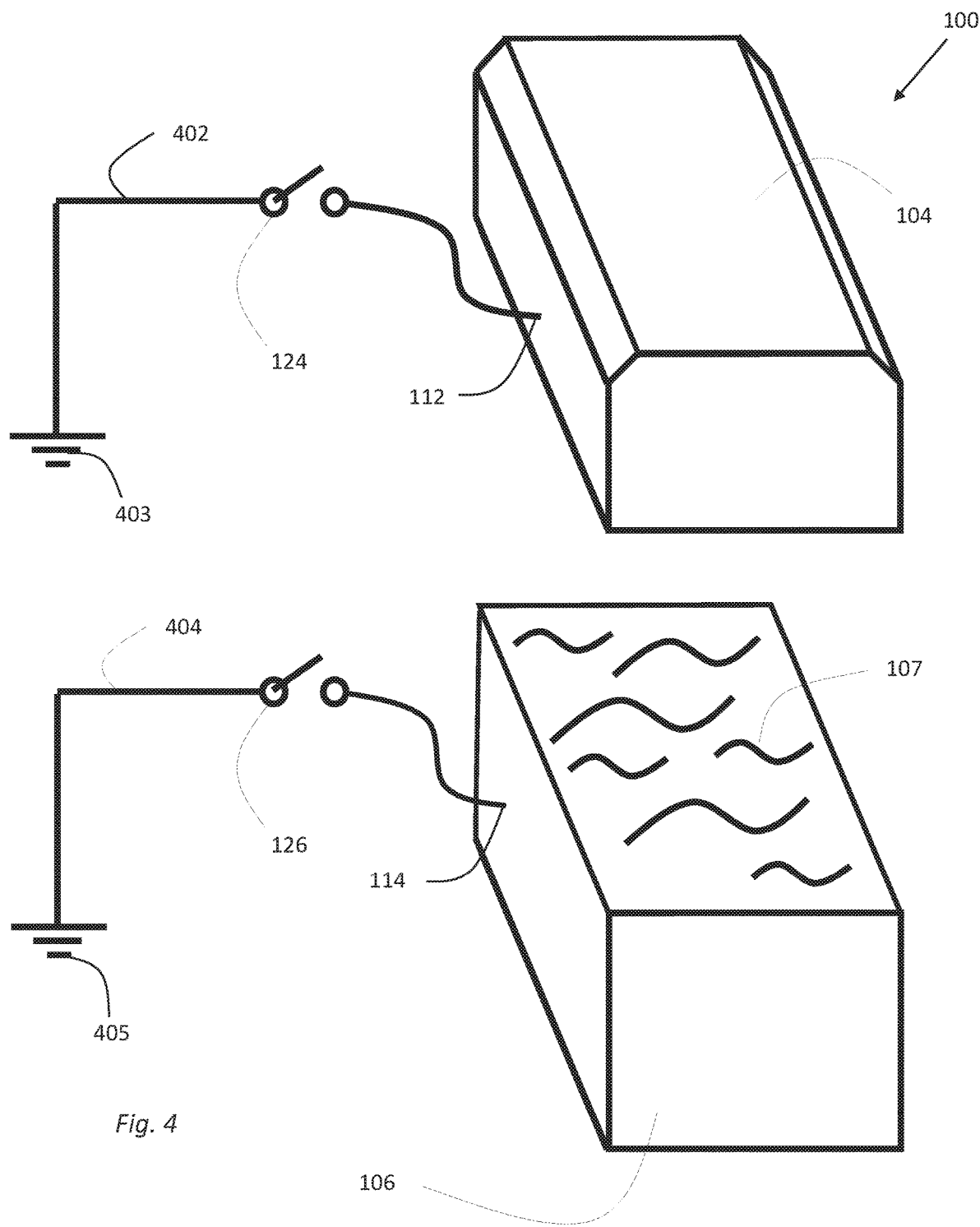
FIG. 4 is a perspective view of an embodiment of an isolation tank showing an alternative grounding circuit.

As noted above, an embodiment having both a shield grounding terminal 112 and a liquid grounding terminal may discharge current to separate or the same physical grounds. For example, as shown in FIG. 3, the shield 110 and liquid 107 may share the same ground path 302 terminating in shared ground 304. Alternatively, as shown in FIG. 4, the grounding paths of the shield 110 and the liquid 107 may be isolated from one another. For example, shield 110 may discharge along grounding path 402 to dedicated ground 403, and the liquid 107 may discharge along grounding path 404 to dedicated ground 405.

The representative embodiments of FIGS. 1, 3 and 4 illustrate that the connections and disconnections to ground can be achieved by one or more switches, providing a user with control over the grounding strategy employed. However, a switch is not the only method to selectively make connections to the ground. Connections to ground could be provided with jumpers, bus bars, removable electrical plugs, removable electrical jacks, direct connections, other electrical connections and the like. For example, the conductive shield 110 could rest on a grounding pad and the fluid ground 114 could be achieved with a freestanding grounding probe placed into the fluid 107.

Figure 5A:
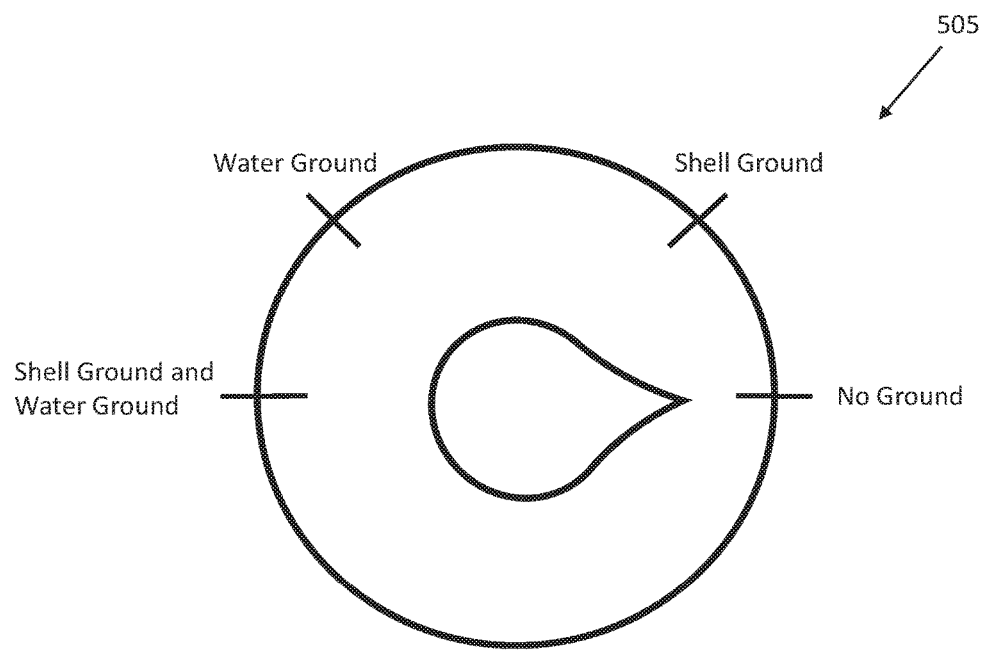
FIGS. 5A and 5B are front elevation views of switches for an isolation tank, in accordance with various embodiments.
Figure 5B:
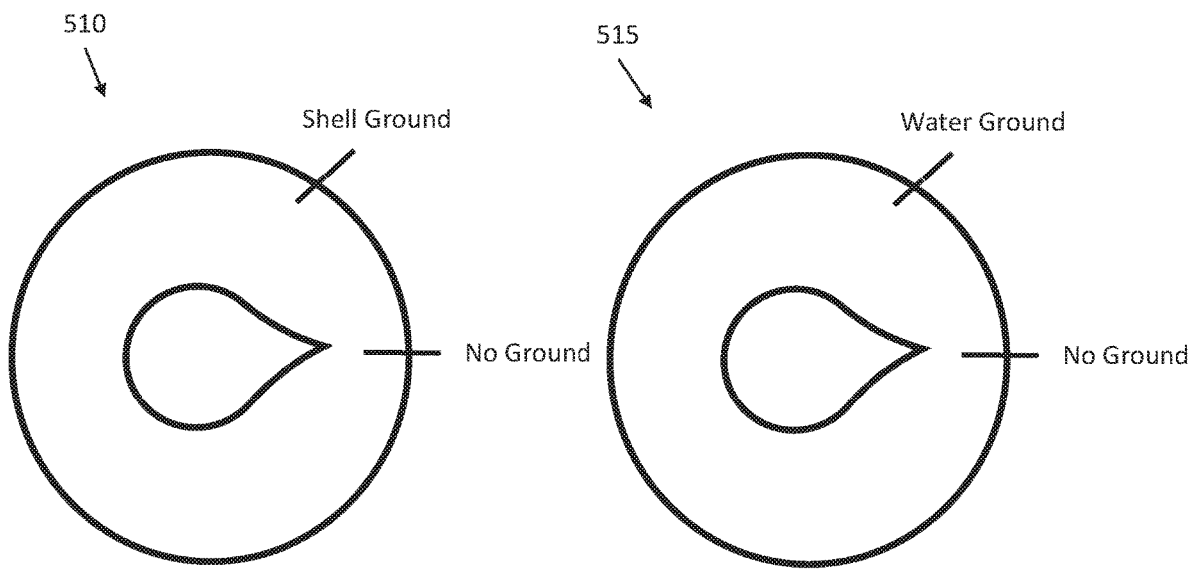

One example of a switch that may be used to provide, disconnect, or connect different grounds is shown in FIG. 5A. in this embodiment, a rotary switch 505 having multiple contacts may be provided on the interior and/or exterior of the tank 100. The rotary switch 505 will allow a user to select which of several possible ground connections to use. FIG. 5A illustrates an embodiment where the shield 110 and liquid 107 share the same grounding path. The rotary switch has switch contacts configured to connect the grounding path 302 to the shield grounding terminal 112 only, the liquid grounding terminal 114 only, both grounding terminals 112, 114, or no grounding terminal. Although a rotary switch is illustrated in FIG. 5A a similar switching strategy could be implemented with one or more toggle switches, digital switching apparatus, relays, or other switching elements.

The switching embodiment of 5B is representative of an isolation chamber 100 having separate dedicated shell and fluid grounds, as illustrated in FIG. 4. In this embodiment, two separate switches, 510 and 515 may be used to connect or disconnect the appropriate ground path to the shield ground terminal 112, or the fluid ground terminal 114. Thus, a user may use the switches 510 and 515 to connect the grounding path 402 to the shield grounding terminal 112 only, connect the grounding path 404 to the liquid grounding terminal 114 only, connect both grounding terminals 112, 114, to the appropriate grounding path, or disconnect both grounding terminals. Although a pair of rotary switches is illustrated in FIG. 5A, a similar switching strategy could be implemented with a single rotary switch having multiple contacts, a ganged rotary switch having multiple levels, an array of toggle switches, digital switching apparatus, relays, or other switching elements.

Furthermore, some or all the grounding switches associated with an isolation chamber 100 may be controlled by an automated system, a remote-control system, or a logically enabled switching system. In one representation of an automated system, shown on FIG. 3, an antenna or sensor 302 and any necessary detection circuitry detects undesirable radiation or the presence of an external EMF. The sensor 302 is in communication with a control system 304 which includes software stored on a non-transient machine readable medium, logic and hardware necessary to process the signal received from the sensor 302 and cause the actuation of electronically implemented switches 124, 126. Thus, the control system 304 autonomously grounds various elements of the isolation chamber 100 only when the sensor and associated circuitry detects undesirable radiation or the presence of an external EMF.

Alternatively, the sensor 302 may be configured to detect and analyze a free radical count associated with the user of the isolation chamber 100, the presence of an electrical charge in the shell 108 or fluid 107, the presence of an electrical or magnetic field in or near the interior of the isolation chamber 100, or any other condition that may trigger the automatic connection of one or more of the shield 110, fluid 107, or user to ground. As noted above, electrical elements such as a heater or pump associated with the isolation chamber 100 will typically be grounded through the household or building ground and a GFI circuit providing some measure of safety. An automated supplemental ground as described above provides additional safety, in the event of a lightning strike or other transient event.

Having described the present invention, it will be understood by those skilled in the art that many changes in construction and widely differing embodiments and applications of the invention will suggest themselves without departing from the scope of the present invention.

Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. An isolation tank comprising:
   a shell comprising an upper cover and a lower tank portion having one or more sidewalls connected to a floor, the lower tank portion configured to hold liquid, and the lower tank portion and the upper cover together defining an interior chamber configured to receive a user;
   a conductive shield operatively associated with at least a portion of the shell and configured to shield at least a portion of the interior chamber from an external electromagnetic field;
   a shield ground electrically coupled to the shield and configured to electrically ground the shield;
   a liquid ground electrically coupled to the liquid contained in the lower tank portion and configured to electrically ground the liquid; and
   a switch configured to switch between at least two of connecting the shield to the shield ground, connecting the liquid to the liquid ground, connecting the shield to the shield ground and connecting the liquid to the liquid ground, disconnecting the shield from the shield ground, disconnecting the liquid from the liquid ground, or disconnecting the shield from the shield ground and disconnecting the liquid from the liquid ground.

2. The isolation tank of claim 1, wherein the isolation tank is configured to isolate the user from external stimulus comprising at least one of sound stimulus, light stimulus, tactile stimulus, or mechanical stimulus.

3. The isolation tank of claim 1, wherein the upper cover comprises a door or hatch.

4. The isolation tank of claim 1, wherein the liquid is at least one of water or water containing a dissolved salt.

5. The isolation tank of claim 1, wherein the liquid is heated to a body temperature of the user.

6. The isolation tank of claim 1, wherein the shield comprises at least one of copper, aluminum, gold, silver, iron, nickel, carbon, or carbon fiber.

7. The isolation tank of claim 1, wherein the shield comprises at least one of a mesh, a mesh cloth, a woven cloth, a sheet, a plurality of wires, a wire grid or a plurality of filaments.

8. The isolation tank of claim 1, wherein the shield is integrated into the shell.

9. The isolation tank of claim 1, wherein the shield is a separate structure from the shell.

10. A method, comprising:
    providing an isolation tank comprising a shell comprising an upper cover and a lower tank portion having one or more sidewalls connected to a floor, the lower tank portion configured to hold liquid, and the lower tank portion and the upper cover together defining an interior chamber configured to receive a user;
    providing a conductive shield operatively associated with at least a portion of the shell and configured to shield at least a portion of the interior chamber from an external electromagnetic field;
    providing a shield ground electrically coupled to the shield and configured to electrically ground the shield;
    providing a liquid ground electrically coupled to the liquid and configured to electrically ground the liquid;
    providing a switch configured to switch between at least two of connecting the shield to the shield ground, connecting the liquid to the liquid ground, connecting the shield to the shield ground and the liquid to the liquid ground, disconnecting the shield from the shield ground, disconnecting the liquid from the liquid ground, or disconnecting the shield from the shield ground and disconnecting the liquid from the liquid ground; and
    switching, via the switch, between at least two of connecting the shield to the shield ground, connecting the liquid to the liquid ground, connecting the shield to the shield ground and the liquid to the liquid ground, disconnecting the shield from the shield ground, disconnecting the liquid from the liquid ground, or disconnecting the shield from the shield ground and disconnecting the liquid from the liquid ground.

11. The method of claim 10, further comprising providing the shield comprising at least one of copper, aluminum, gold, silver, iron, nickel, carbon, or carbon fiber.

12. The method of claim 10, further comprising providing the shield comprising at least one of a mesh, a mesh cloth, a woven cloth, a sheet, a plurality of wires, or a plurality of filaments.

* * * * *